United States Patent
Walzman (10) Patent No.: US 11,660,111 B2
(45) Date of Patent: *May 30, 2023

(54) ALTERNATIVE USE FOR HYDROGEL INTRASACCULAR OCCLUSION DEVICE WITH VERTICALLY ORIENTED REINFORCEMENT MEMBERS FOR STRUCTURAL SUPPORT

(71) Applicant: Daniel Ezra Walzman, Bergenfield, NJ (US)

(72) Inventor: Daniel Ezra Walzman, Bergenfield, NJ (US)

(*) Notice: Subject to any disclaimer, the term of this patent is extended or adjusted under 35 U.S.C. 154(b) by 331 days.

This patent is subject to a terminal disclaimer.

(21) Appl. No.: 16/783,000

(22) Filed: Feb. 5, 2020

(65) Prior Publication Data

US 2020/0187978 A1 Jun. 18, 2020

Related U.S. Application Data (60) Continuation-in-part of application No. 15/732,399, filed on Nov. 7, 2017, now abandoned, which is a
(Continued)

(51) Int. Cl.
*A61B 17/12* (2006.01)
*A61B 17/3207* (2006.01)
(Continued)

(52) U.S. Cl.
CPC ........... *A61B 17/320758* (2013.01); *A61B 17/1214* (2013.01); *A61B 17/1219* (2013.01);
(Continued)

(58) Field of Classification Search
CPC .......... A61B 17/12181; A61B 17/1214; A61B 17/12113; A61B 17/12177;
(Continued)

(56) References Cited

U.S. PATENT DOCUMENTS

| | | |
|---|---|---|
| 3,874,388 A | 4/1975 | King et al. |
| 4,282,875 A | 8/1981 | Serbinenko et al. |

(Continued)

FOREIGN PATENT DOCUMENTS

| | | |
|---|---|---|
| WO | WO1997002811 A1 | 1/1997 |
| WO | WO2011057002 A2 | 5/2011 |

OTHER PUBLICATIONS

Fujita S, Tamai H, Kyo E, et al. New technique for superior guiding catheter support during advancement of a balloon in coronary angioplasty: The anchor technique. Catheter Cardiovasc Interv 2003;59:482-488.
(Continued)

*Primary Examiner* — George J Ulsh
(74) *Attorney, Agent, or Firm* — Harris Beach PLLC (57) ABSTRACT

A device for endovascular treatment to ameliorate aneurysm recurrences by deploying a treatment mesh having a plurality of vertically oriented elongated support reinforcement elements that are substantially parallel and oriented upon a plane in communication with the mesh. Upon deployment, the array of distal ends of the support extensions and reinforcements are substantially oriented upon a plane, which plane is in substantially the same orientation as the opening of the aneurysm into which the device was deployed. The treatment mesh may incorporate a coating of hydrogel, optionally impregnated with pharmaceutical compounds.

20 Claims, 3 Drawing Sheets

Related U.S. Application Data division of application No. 15/732,365, filed on Oct. 30, 2017, now Pat. No. 10,448,970.

(60) Provisional application No. 62/497,851, filed on Dec. 5, 2016.

(51) Int. Cl.

| | | |
|---|---|---|
| *A61F 2/852* | (2013.01) | |
| *A61F 2/91* | (2013.01) | |
| *A61L 29/14* | (2006.01) | |
| *A61L 31/02* | (2006.01) | |
| *A61L 31/04* | (2006.01) | |
| *A61L 31/10* | (2006.01) | |
| *A61L 31/12* | (2006.01) | |
| *A61L 31/14* | (2006.01) | |
| *A61L 31/16* | (2006.01) | |
| *A61B 17/22* | (2006.01) | |
| *A61B 17/00* | (2006.01) | |
| *A61B 90/00* | (2016.01) | |
| *A61F 2/82* | (2013.01) | |
| *A61L 29/16* | (2006.01) | |
| *A61M 25/10* | (2013.01) | |
| *A61M 25/00* | (2006.01) | |

(52) U.S. Cl.
CPC .............. *A61B 17/12031* (2013.01); *A61B 17/12113* (2013.01); *A61B 17/12172* (2013.01); *A61B 17/12177* (2013.01); *A61F 2/852* (2013.01); *A61F 2/91* (2013.01); *A61L 29/145* (2013.01); *A61L 31/022* (2013.01); *A61L 31/04* (2013.01); *A61L 31/10* (2013.01); *A61L 31/125* (2013.01); *A61L 31/14* (2013.01); *A61L 31/145* (2013.01); *A61L 31/146* (2013.01); *A61L 31/16* (2013.01); *A61B 17/12122* (2013.01); *A61B 17/22032* (2013.01); *A61B 2017/00477* (2013.01); *A61B 2017/00867* (2013.01); *A61B 2017/00893* (2013.01); *A61B 2017/00898* (2013.01); *A61B 2017/1205* (2013.01); *A61B 2017/1209* (2013.01); *A61B 2017/320716* (2013.01); *A61B 2090/3966* (2016.02); *A61B 2217/005* (2013.01); *A61B 2217/007* (2013.01); *A61F 2002/823* (2013.01); *A61F 2002/826* (2013.01); *A61F 2220/0033* (2013.01); *A61F 2250/0063* (2013.01); *A61L 29/16* (2013.01); *A61L 2430/06* (2013.01); *A61M 25/10* (2013.01); *A61M 2025/0057* (2013.01); *A61M 2210/125* (2013.01)

(58) Field of Classification Search
CPC .............. A61B 17/22032; A61L 29/145; A61L 29/16; A61M 2025/0057; A61M 2210/125
See application file for complete search history.

(56) References Cited

U.S. PATENT DOCUMENTS

| | | |
|---|---|---|
| 4,346,712 A | 8/1982 | Handa et al. |
| 4,402,319 A | 9/1983 | Handa et al. |
| 4,619,246 A | 10/1986 | Mølgaard-Nielsen et al. |
| 4,675,361 A | 6/1987 | Ward |
| 5,135,516 A | 8/1992 | Sahatjian et al. |
| 5,165,421 A | 11/1992 | Fleischacker et al. |
| 5,263,963 A | 11/1993 | Garrison et al. |
| 5,334,210 A | 8/1994 | Gianturco |
| 5,733,294 A | 3/1998 | Forber et al. |
| 5,907,893 A | 6/1999 | Zadno-Azizi et al. |
| 6,221,086 B1 | 4/2001 | Forber |
| 6,375,670 B1 | 4/2002 | Greenhalgh |
| 6,605,102 B1 | 8/2003 | Mazzocchi et al. |
| 7,128,736 B1 | 10/2006 | Abrams et al. |
| 7,575,582 B2 | 8/2009 | Gandhi et al. |
| 8,658,147 B2 | 2/2014 | Sannino et al. |
| 2003/0012816 A1 | 1/2003 | West et al. |
| 2007/0078480 A1 | 4/2007 | Belenkaya et al. |
| 2008/0033341 A1 | 2/2008 | Grad |
| 2008/0208317 A1 | 8/2008 | Jang et al. |
| 2010/0069948 A1 | 3/2010 | Veznedaroglu et al. |
| 2010/0324665 A1 | 12/2010 | Shaw et al. |
| 2011/0144669 A1 | 6/2011 | Becking et al. |
| 2011/0152993 A1 | 6/2011 | Marchand et al. |
| 2012/0158034 A1 | 6/2012 | Wilson et al. |
| 2012/0283811 A1 | 11/2012 | Neilan |
| 2013/0211495 A1 | 8/2013 | Halden et al. |
| 2016/0120551 A1 | 5/2016 | Connor |
| 2016/0249935 A1 | 9/2016 | Hewitt et al. |
| 2017/0245864 A1 | 8/2017 | Franano et al. |

OTHER PUBLICATIONS

Di Mario C. Techniques to enhance guide catheter support. Catheter Cardiovasc Interv 2008;72:505-512.

Mahmood, A. Applications of the Distal Anchoring Technique in Coronary and Peripheral Interventions Cath Lab Digest Oct. 2011 vol. 19—Issue 10.

C. Di Mario et al., "Techniques to Enhance Guide Catheter Support," Catheterization and Cardiovascular Interventions, vol. 72, No. 4, Jun. 16, 2008, Introduction Only, 3 pages.

S. Fujita et al., "New Technique for Superior Guiding Catheter Support During Advancement of a Balloon in Coronary Angioplasty: The Anchor Technique," Catheterization and Cardiovascular Interventions, vol. 59, No. 4, Jul. 25, 2003, Abstract Only, 2 pages.

A. Mahmood et al., "Applications of the Distal Anchoring Technique in Coronary and Peripheral Interventions," Journal of Invasive Cardiology, vol. 23, 2011, 6 pages.

ALTERNATIVE USE FOR HYDROGEL INTRASACCULAR OCCLUSION DEVICE WITH VERTICALLY ORIENTED REINFORCEMENT MEMBERS FOR STRUCTURAL SUPPORT

CROSS-REFERENCES

This continuation-in-part application claiming priority to U.S. utility application Ser. No. 15/932,399, which claims priority to provisional patent application Ser. No. 62/497,851 filed Dec. 5, 2016 (5 Dec. 2016) for a "Hydrogel Intrasaccular Occlusion Device" (Walzman) and to non-provisional patent application Ser. No. 15/732,365 filed Oct. 30, 2017 (30 Oct. 2017) for an "Alternate use for Hydrogel Intrasaccular Occlusion Device".

FEDERALLY FUNDED R&D

None

BACKGROUND OF THE INVENTION

Field of the Invention

The present disclosure relates to the field of endovascular treatment. More particularly, the present invention uses a modified hydrogel intrasaccular occlusion device tool designed to implement an endovascular treatment to facilitate aneurysm treatment while ameliorating or eliminating aneurysm recurrence.

Background Art

The present invention is a device for use with an intrasaccular occlusion tool to safely and effectively implement an endovascular treatment of aneurysms while ameliorating or eliminating aneurysm recurrence. The prior art includes endovascular devices that have provided high density, mesh-like metallic materials across the aneurysm neck, in place of coil technology. It has also taught in vivo preclinical performance of a self-expanding intrasaccular embolization device (see Preliminary Results of the Luna Aneurysm Embolization System in a Rabbit Model: A New Intrasaccular Aneurysm Occlusion Device by S. C. Kwon in the American Journal of Neuroradiology A.INR 201 1 32: 602-606). While the devices identified in the prior art achieved high rates of complete angiographic occlusion, medical difficulties still arose due to inadvertent and/or unintended fluid exchange at and for near the site where the devices noted in the prior art were used. Recent data has shown the web devices have been associated with a very high rate of aneurysm recurrence, as high as 20 to 60 percent.

For example, the Woven EndoBridge (WEB) is a novel device for the treatment of wide-necked intracranial bifurcation aneurysms. As reported by Clajus in J NeuroIntervent Surg (doi:10.1136/neurintsurg-2016-012276) in an article titled "Initial and mid-term results from 108 consecutive patients with cerebral aneurysms treated with the WEB device" the value of webbing generally and WEB in particular, was demonstrated when reporting 'real-world experience' in the use of all iterations of WEB devices (available in Europe) in ruptured and unruptured aneurysms.

Other references of note include:
U.S. Pat. No. 3,874,388, filed Feb. 12, 1973, published Apr. 1, 1975 Ochsner Med Found Alton Shunt defect closure system;
U.S. Pat. No. 4,282,875, filed Jan. 24, 1979, published Aug. 11, 1981 Serbinenko Fedor A. Occlusive device;
U.S. Pat. No. 4,346,712, filed Feb. 13, 1980, published Aug. 31, 1982 Kuraray Company, Ltd. Releasable balloon catheter;
U.S. Pat. No. 4,402,319, filed Dec. 30, 1981, published Sep. 6, 1983 Kuraray Co., Ltd. Releasable balloon catheter
U.S. Pat. No. 4,619,246, filed May 20, 1985, published Oct. 28, 1986 William Cook, Europe A/S Collapsible filter basket;
U.S. Pat. No. 4,675,361, filed Jun. 24, 1983, published Jun. 23, 1987 Thoratec Laboratories Corp. Polymer systems suitable for blood-contacting surfaces of a biomedical device, and methods for forming;
U.S. Pat. No. 5,165,421, filed Jul. 20, 1990, published Nov. 24, 1992 Lake Region Manufacturing Co., Inc. Hollow lumen cable apparatus;
U.S. Pat. No. 5,263,963, filed Apr. 8, 1991, published Nov. 23, 1993 Advanced Cardiovascular Systems, Inc. Expandable cage catheter for repairing a damaged blood vessel;
U.S. Pat. No. 5,334,210, filed Apr. 9, 1993, published Aug. 2, 1994 Cook Incorporated Vascular occlusion assembly;
U.S. Pat. No. 5,733,294, filed Feb. 28, 1996, published Mar. 31, 1998 B. Braun Medical, Inc. Self-expanding cardiovascular occlusion device, method of using and method of making the same;
U.S. Pat. No. 5,907,893, filed Jan. 31, 1997, published Jun. 1, 1999 Medtronic, Inc. Methods for the manufacture of radially expansible stents;
U.S. Pat. No. 6,221,086, filed May 18, 1999, published Apr. 24, 2001 B. Braun Medical Sas Covered self-expanding vascular occlusion device;
U.S. Pat. No. 6,375,670, filed Aug. 25, 2000, published Apr. 23, 2002 Prodesco, Inc. Intraluminal filter;
U.S. Pat. No. 6,605,102, filed Nov. 12, 1996, published Aug. 12, 2003 Ev3, Inc. Intravascular trap and method of trapping particles in bodily fluids;
U.S. Pat. No. 7,575,582, filed May 16, 2006, published Aug. 18, 2009 Micrus Corporation Apparatus for deployment of micro-coil using a catheter;
US2008/0033341, filed Aug. 6, 2007, published Feb. 7, 2008 Bay Holdings Ltd. Methods and devices for reducing or blocking blood flow to a selected blood vessel or part thereof;
US2010/0069948, filed Sep. 11, 2009, published Mar. 18, 2010 Micrus Endovascular Corporation Self-expandable aneurysm filling device, system and method of placement; and
WO2011/057002 A2, filed Nov. 4, 2010, published May 12, 2011 Sequent Medical Inc. Multiple layer filamentary devices or treatment of vascular defects.

The two most frequent ways that web devices fail and thereby result in an aneurysm recurrence are (1) web device collapse and/or compression and (2) distal migration of the web device into the aneurysm. Additionally, in a ruptured aneurysm there is concern the aneurysm does not close and/or thrombose quickly enough with web devices, which has sometimes resulted in recurrent aneurysm rupture after treatment. The present invention is an alternative use for hydrogel intrasaccular occlusion devices, which is capable of ameliorating said two most frequent web device failures.

The prior art includes "Left atrial appendage occlusion device," WO 2013/126523 A1 (Erzberger et al.), a device known as Watchman. This is a type of left atrial appendage (LAA) closure technology consisting of a delivery catheter and a device that is permanently implanted in the LAA of the heart. This device prevents LAA blood clots from entering the bloodstream and potentially causing a stroke.

The Watchman device is generally associated with high cost, with a U.S. list price of $23,500 for each device, and $1,500 for each delivery system.

The Watchman device is currently delivered through a 14 Fr (Trench'-Fr-3 Fr=1 mm. diameter) delivery system, and requires a hole of 14 Fr or larger to be made in the femoral vein and the atrial septum for delivery. The larger the hole, the more risk of complication. Said risk includes the risk of stroke associated with atrial fibrillation. The present invention offers a method of serving the same purpose as a Watchman but with a dramatically smaller hole.

Endovascular surgery is a minimally invasive procedure used to treat problems affecting the blood vessels, such as an aneurysm, which is a swelling or "ballooning" of the blood vessel. The surgery typically involves making a small incision near each hip to access the blood vessels.

Endovascular procedures may result in endo-leaks. Such endo-leaks typically involve continued flow of blood outside a covered stent. Unwanted flow is maintained between the outside of the covered stent and the vessel wall, including the aneurysm sac and/or a fistula, if those are the pathologies being covered/treated, respectively. This results in continued filling of blood with continued associated risk to the patient. These endo-leaks occur most often from one of two causes (+/−combination of the two). 1. There can be poor apposition of the wall of the covered stent to the vessel wall, most often at the ends of the stent, especially the proximal end (the end from which blood flow comes). This results in continued flow of blood between the stent and the vessel wall, outside the stent. 2. In some large aneurysms, such as aortic aneurysms, the aneurysm crosses multiple vessel branches, and so when a covered stent is used to treat the aneurysm, these branches are covered. Often some of these branches will start to flow retrograde, and the aneurysm sac can continue to fill. It can even continue to expand and/or rupture.

Endo-leaks can be caused by many factors. Some, such as incorrectly sized stents, can be corrected. Others, such as irregular vessels, branches feeding behind the covered stent (as above), and bends in the vessel at the ideal stent landing zone, often cannot be easily ameliorated.

One possible solution to eliminate or ameliorate endo-leaks may be implemented as follows: the outside of the covered stent can be lined with an adhered hydrogel, that once implanted, will expand to fill any potential spaces between the vessel wall and the material of the covered stent, thus closing any potential persistent channels outside the stent.

A second possible solution to eliminate or ameliorate endo-leaks may be implemented as follows: the outside of the covered stent can be lined with an adhered hydrogel, that once implanted, will expand to fill any potential spaces between the vessel wall and/or the wall of the aneurysm sac the stent is treating, including the material of the covered stent, thus closing the aneurysm sac and preventing further flow into it.

A third possible solution to eliminate or ameliorate endo-leaks may be implemented as follows: combining the two-implementation noted above.

These three solutions may be implemented with existing stent structure because most covered stents consist of Dacron or Polyester and thus suitable for covering with hydrogel.

Stents and other endovascular devices have issues in that they are thrombogenic when they are first inserted, until they are incorporated into the vessel and endothelialized in some cases such as mechanical cardiac valves, forever. This results in significant rates of thrombotic complications, including thrombosed vessels resulting in stroke, myocardial infarction, or other ischemic complications. In order to minimize such risks, patients are routinely started on anti-platelet therapy, often dual antiplatelet therapy, with agents such as Plavix or Brilinta, and aspirin. In addition, other endovascular devices, particularly those implanted in the heart, such as mechanical heart valves, tend to cause a different type of clot that necessitates the use of anticoagulants to protect against clot formation. Although the medications reduce the rate of clot formation, they do not eliminate clot formation altogether, and patients can still suffer complications from clotting. Additionally, all these medications have significant rates of bleeding complications. Hydrogel is more inert and does not cause thrombus formation/induction.

Additionally, stent and other foreign body devices when implanted in the body cause a local tissue reaction that can result in local tissue overgrowth. This can result in the development of in-stent stenosis or other issues with scarring. Hydrogel is more inert, and would reduce such tissue reaction, if the hydrogel instead was in contact with the local tissue.

The present invention teaches placing a thin coating of hydrogel on the entire surface of any endovascular device exposed to the inner surface of the blood vessel and/or blood products.

The present invention also teaches placing a thin layer (one (1) nanometer to one (1) centimeter) of hydrogel over a portion of such a device as well. Do so will reduce but not completely eliminate the risk of thrombus formation. By completely covering these devices with the thin layer of hydrogel a significantly reduce the rate of thrombus formation may be achieved. This will also reduce the need for anti-platelet and or anticoagulant.

The reduction in the use of anti-platelet and/or anticoagulant is a non-obvious benefit of the use of hydrogel as taught above because anti-platelet and anticoagulant medications have significant associated morbidity. By eliminating the need for them we can reduce said morbidity further. The hydrogel coating would also reduce the tissue reaction and associated complications such as in-stent stenosis.

The hydrogel can also simultaneously fill any spaces between said stent and the vessel wall, reducing the incidence of endo-leaks, while also helping secure the stent in place, reducing the incidence of stent migration.

Advantages of the Current Invention

The present invention substantially fulfills the forgoing unmet needs. A gel is a solid jelly-like material that can have properties ranging from soft and weak to hard. A hydrogel is a network of polymer chains that are hydrophilic, sometimes found as a colloidal gel in which water is the dispersion medium. These may be woven and/or adhered to the metal structures. In addition to aiding the wound treatment hydrogel has been shown to offer relief from pain for hours after application. Furthermore, the expansion of the hydrogel after it is implanted into the body may increase the coverage of a metal mesh implanted and thereby decrease permeability of blood into the aneurysm, promoting faster thrombosis and healing of the aneurysm.

Hydrogel dressings consist of 90 percent water in a gel base, and serve to help monitor fluid exchange from within the wound surface. The application of hydrogel assists in protecting areas adversely affected during endovascular treatments from wound infection and promotes efficient healing. Hydrogel dressings generally come in three different forms (which constitute various release mechanisms), including: amorphous hydrogel: a free-flowing gel, distributed in tubes, foil packets and spray bottles; impregnated hydrogel: typically saturated onto a gauze pad, nonwoven sponge ropes and/or strips; and sheet hydrogel: a combination of gel held together by a thin fiber mesh.

A study published in the Journal of the American College of Cardiology: Basic to Translational Science, reported that an inject-able gel can maintain its healing characteristics. In particular, rebuilding of muscular structures was reported from a gel originally derived from a pig's cardiac muscle tissue, which was stripped of cells until all that was left was an extracellular matrix. A 2010 study in the Journal of Cell Science noted that an element of gel used in the aforementioned Journal of the American College of Cardiology study was responsible for tissue regeneration and re-growth: One non-limiting version of a hydrogel that expands in the body is a co-polymer of acrylamide and sodium acrylate cross linked.

The present disclosure relates to the field of endovascular treatment. More particularly, the present invention modifies a hydrogel intrasaccular occlusion device such as disclosed in provisional patent application Ser. No. 62/497,851, by providing expanded hydrogel which extends outside the device, on the sides of the device, and inside the device. Such modifications are designed to implement an endovascular treatment to ameliorating or eliminating aneurysm recurrence. The existing hydrogel intrasaccular occlusion device tool such as disclosed in provisional patent application Ser. No. 62/497,851 envisions adding a hydrogel to a mesh-like saccular aneurysm embolization device, such as the Sequent Web, the Luna Aneurysm Embolization system or similar devices or systems. Once done and deployed in the body, the hydrogel expands and further decreases the permeability of the device to blood. This can facilitate more immediate thrombosis of the aneurysm, resulting in more immediate reduction in the risk of the aneurysm rupturing.

The present invention can be used to close an LAA. It has specific advantages when compared to the Watchman device. In particular, the Watchman is delivered through a "transseptal" approach, coming from the femoral vein, into right atrium of the heart, and across the atrial septum (a hole needs to be made) and into the left atrium, from where the left atrial appendage is then accessed. The current Watchman is delivered through a 14Fr system. Thus, compared to the present invention, a much larger hole in the femoral vein, with corresponding increased risk of bleeding complications and/or vessel injury must be made. Additionally, a much smaller hole in the septum can be used for access if implanting the present invention in the left atrial appendage, via a transseptal approach, instead of the Watchman. The present invention can be delivered through systems smaller than 4Fr (sometimes as small as 2Fr; but probably not that small for the 21-33 mm wide device needed in the left atrial appendage). The current invention can be delivered in appropriate sizes through systems from 2Fr to 11Fr.

The present invention is capable of larger webs that can easily be delivered through catheters considerably smaller than the current 14Fr Watchman. This will allow the current invention to be more effective in eliminating or ameliorating blood clots from entering the bloodstream and potentially causing a stroke.

The present invention uses a device designed to facilitate endovascular treatment by adding hydrogel along the metal struts/web of the device and using it to prevent episodes of distal migration due to the addition of the hydrogel. This is achieved by providing expanded hydrogel which extends outside the device and on the sides of the device. The extensions will help "grip" the aneurysm walls and minimize the incidence of migration. Additionally, the extensions help speed thrombosis and minimize risk of collapse. The center open space within the web can have added strands and/or struts and/or bars of hydrogel. The extensions can be oriented vertically for added support, to further minimize the risk of device collapse.

The present invention in all embodiments will be partially or fully covered by a thin coating of hydrogel. Said coating acts as both a medication delivery system and a barrier to reduce the thrombogenicity of the stent, reducing thrombotic complications, and reducing the need for antiplatelets (with their associated potential hemorrhagic complications—especially in patients with a recent bleed in their brain).

The present invention teaches the affixation of at least one hydrogel layer that expands in vivo to any or all surfaces of a mesh intrasaccular device made of at least one material adapted to close an outpouching in the body such as an aneurysm, the left atrial appendage, or diverticulae of other organs. For purposes of this invention, hydrogel coating will be in a non-hydrated state and will expand in use, upon exposure to bodily fluid.

The current device may be used to treat both venous and arterial aneurysms. It may be used in the brain, the peripheral vasculature, and the arterial vasculature.

BRIEF DESCRIPTION OF THE DRAWINGS

The invention will be better understood and objects other than those set forth above will become apparent when consideration is given to the following detail description thereof. Such description makes reference to the annexed drawings wherein.

The hydrogel coating (22) depicted as mis-formed circles or beads in the foregoing figures is representative only, and the mis-formed circles shown are not drawn to scale. Nor is the hydrogel coating (22) that completely covers an entire device or delivery system shown.

DETAILED DESCRIPTION OF THE INVENTION AND METHOD OF USE

The present disclosure teaches the placement of amorphous hydrogel (22) within or coating surfaces of intrasaccular occlusion devices, which are delivered proximally to target vessels using wire delivery systems (12). Said intrasaccular occlusion devices are typically housed in intrasaccular tools during the transport process.

Coating said intrasaccular occlusion devices, particularly an extension such as treatment mesh (20), allows for the implementation of a therapeutic endovascular treatment.

The amorphous hydrogel (22) is adhered to select surfaces of said device (20) designed to implement an endovascular treatment and may be contained by said device during the endovascular treatment. Alternatively, the amorphous hydrogel (22) is adhered to select surfaces of said device (20) designed to implement an endovascular treatment or is contained by said device designed to implement an endovascular treatment. These alternatives are not necessarily mutually exclusive.

When the coated device designed to implement an endovascular treatment is proximately positioned at the treatment point, and the metal mesh device (2), such as the Sequent Web or Luna Aneurysm Embolization system or similar system, is deployed in the body, the exposure of the adhered added hydrogel with the device to the blood and temperature in the body causes it to further expand. This further decreases the permeability of the device to blood and promoting more immediate thrombosis of the aneurysm or other vascular outpouching, which results in more immediate decrease in the risk of the aneurysm rupturing or clots forming and embolizing.

The present invention uses a device designed to facilitate endovascular treatment by coating hydrogel along the metal struts/web of the device and uses it to prevent episodes of distal migration due to addition of hydrogel. This is achieved by providing expanded hydrogel extends outside the device on the sides of the device. Said extensions will help "grip" the aneurysm walls and minimize the incidence of migration. Additionally, said extensions help speed thrombosis and minimize risk of collapse. The center open space within the web can have added strands and/or struts and/or bars of hydrogel as well. Said extensions can be oriented vertically for added support. Said extensions can be oriented in either direction as well.

More particularly, said extensions which may be made of hydrogel coated metal, metal alloys, or plastic, or other stiff material. All said reinforced elements may be further enhanced by the addition of additional hydrogel proximal to said reinforcement elements.

The present invention can be used with hydrogel. Each embodiment may be used to treat brain aneurysms and heart ailments.

The preferred embodiment would include substantially parallel, vertically oriented elongated support extensions and reinforcements attached or woven into the treatment mesh. However, the vertically oriented support extensions and reinforcements may be attached to or imbedded into the inside of the treatment mesh, outside of the treatment mesh, or both inside and outside of the treatment mesh. Upon deployment of the substantially parallel vertically oriented support extensions and reinforcements, the substantially parallel vertically oriented support extensions and reinforcements would curve to conform to the shape of said treatment mesh. Also, upon deployment, the array of distal ends of the substantially parallel vertically oriented support extensions and reinforcements are substantially oriented upon a plane. The plane has substantially the same orientation as the opening of the aneurysm into which the device was deployed. The vertically oriented support extensions and reinforcements may be attached or joined to the treatment mesh via ties, spot welds, pocket enclosures, biocompatible adhesive, or any other technique known in the art for affixing elements of surgical implant devices.

All of the above extensions may be added with a hydrogel coating on all parts. All of the above extensions may be added with a hydrogel coating on some parts. In some embodiments, all of the above extensions may be added without a hydrogel coating on some parts. In some embodiments, any of the above extensions may be added without any hydrogel coating at all.

All of the above extensions may be covered in a thin coating of hydrogel on the entire surface of any endovascular device exposed to the inner surface of the blood vessel and/or blood products, by placing a thin layer of hydrogen over a portion of such a device as well.

In the preferred embodiment of the current invention, endovascular devices that can be covered with such a layer of hydrogel include metal stents, covered stents, cardiac valves, left atrial appendage occlusion devices such as the Watchman, intra-saccular aneurysm devices, pressure monitors, wires/Leeds, etc. In short, all surfaces of the present invention and devices which deploy the present invention would be covered with a thin layer of hydrogel and thereby covering all metals, and/or plastics, and/or polyesters, and/or Dacron surfaces.

In the preferred embodiment of the current invention a thin coating of hydrogel is placed on all surfaces, including the surface pressing on the vessel wall, it will reduce the rate of intimal hyperplasia caused by the vessel reacting to the foreign body. This result is also a non-obvious benefit of the use of hydrogel because intimal hyperplasia causes vessel narrowing and/or occlusions, which in turn causes suboptimal outcomes, including in some case the death of the patient.

In the preferred embodiment of the current invention, a thin coating of hydrogel is placed on all surfaces of all devices which deliver the claim 1 devices (an extension element for an intrasaccular occlusion tool designed to ameliorate aneurysm recurrences by deploying an amorphous hydrogel) The hydrogel may be use to both prevent blood metal thrombosis and as a delivery mechanism for medications, which can be an immediate release or controlled sustained slow release (embedded in stents or other devices).

For example, hydrogel lining to nonvascular stents, in some embodiments, include biliary and ureter stents which may also reduce rates of in stent stenosis; and may help anchor the stent in place and prevent stent migration.

In some embodiments of the current invention, coatings in addition to a thin coating of hydrogel are added to said thin coating of hydrogel. Said additional coating additives embed said thin coating of hydrogel with compounds for local delivery, short release or sustained release.

In some embodiments, the additional coating include chemotherapy compounds in said thin coating of hydrogel. Said chemotherapy compounds embedded in a device may be use in the carotid artery for a brain tumor in that vascular distribution, or in the right renal artery for a right kidney tumor, or in right pulmonary artery for a right lung mass: this could allow sustained delivery locally, while minimizing the systemic dose and associated side effects.

Said hydrogel thin coating may be impregnated with pharmaceutical compounds. Said compounds may include, but are not limited to nimodipine, verapamil, Cardene, nitroglycerin, and nitroprusside. Said compounds may be formulated for immediate release or controlled sustained slow release.

Alternatively, to minimize the risk of severe symptomatic vasospasm in aneurysmal subarchnoid hemorrhage (a typical bleed from a ruptured brain aneurysm), the thin coating of hydrogel might include a vasodilator compound that slowly releases over 3 weeks, and can be embedded in a stent for placement in the common or internal carotid arteries on both sides, including the placement in one or both vertebral arteries. Non-limiting examples of vasodilators that can be embedded include nimodipine, verapamil, Cardene, nitroglycerin, and nitroprusside.

Figure 1:
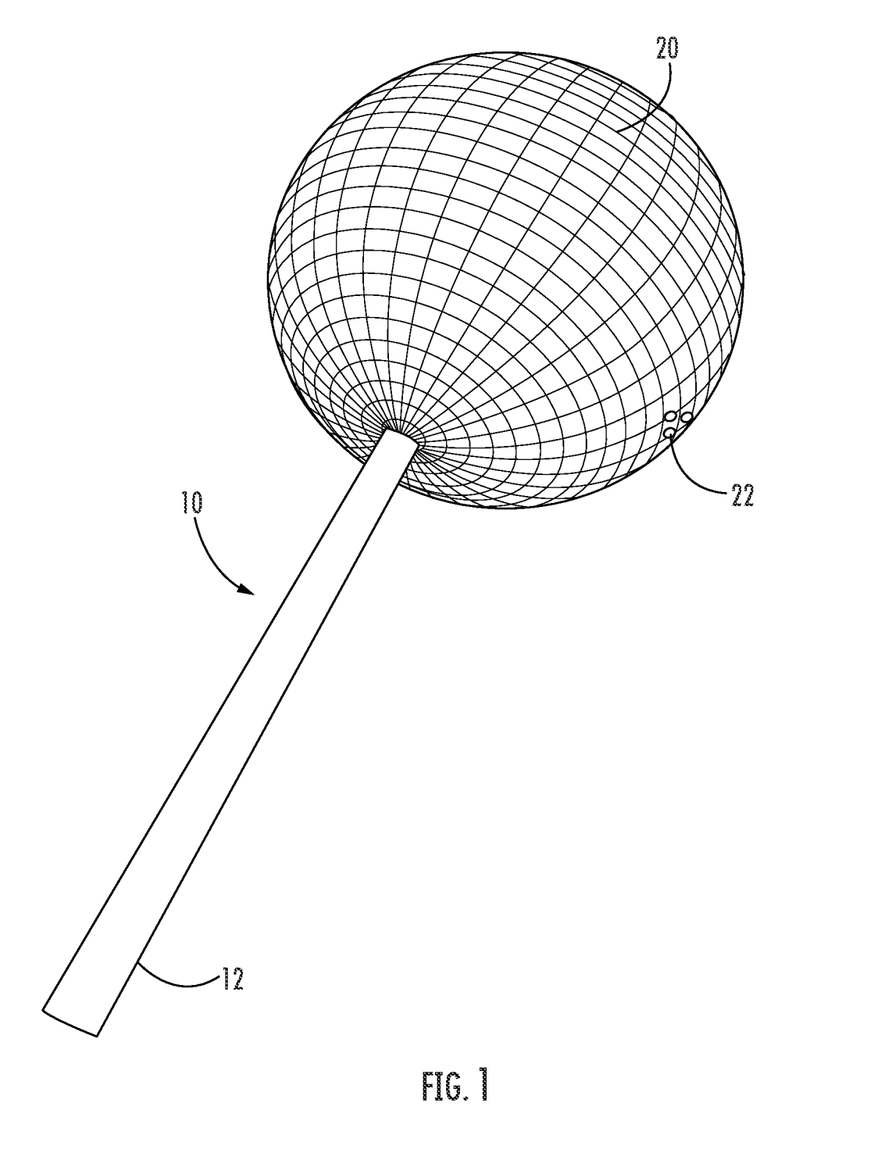
FIG. 1 illustrates at a distal end of a wire is a deployed device designed to implement an endovascular treatment mesh at a treatment site with hydrogel coating.
Figure 2:
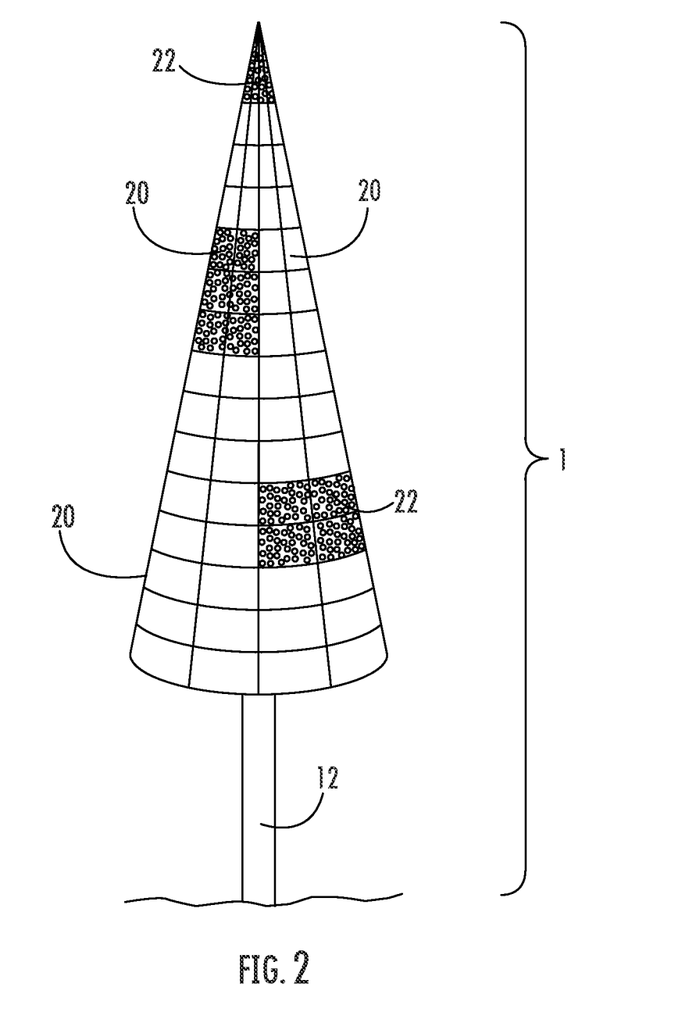
FIG. 2 illustrates at a distal end of wire (12) is an un-deployed device designed to implement an endovascular treatment mesh with a hydrogel coating.

As more particularly shown in FIG. 1, delivery wire (12) with mesh device (20) disposed at the distal end of said wire (12). An embodiment of treatment mesh (20) is substantially spherical or circumferential upon deployment. A preferred embodiment of treatment mesh (20) is designed to be implemented at a treatment site with a hydrogel coating (22). Deployed device (10) is distally attached to a delivery system which may be as simple as a wire (12) but may be an intravascular tool (not shown) such as a nonvascular stent. In the preferred embodiment, such delivery tools would also be coated with a thin coating of hydrogel (22), preferably having a thickness of one nanometer to one centimeter. Said thickness is determined by the internal diameter of the target area, and the outer dimension of treatment mesh (20). FIG. 2 depicts the same treatment mesh (20) prior to deployment, as well as wire (12). The coating must be sufficiently thin so that the un-hydrated hydrogel (22) will allow treatment mesh (20) to proceed proximally to the target area in an undeployed state. For example, if the internal target area of the vessel has a diameter of 1.1 cm, and the largest dimension of the undeployed mesh (20) is one centimeter, then the preferred thickness of the hydrogel (22) coating for this situation is 0.1 cm.

Figure 3:
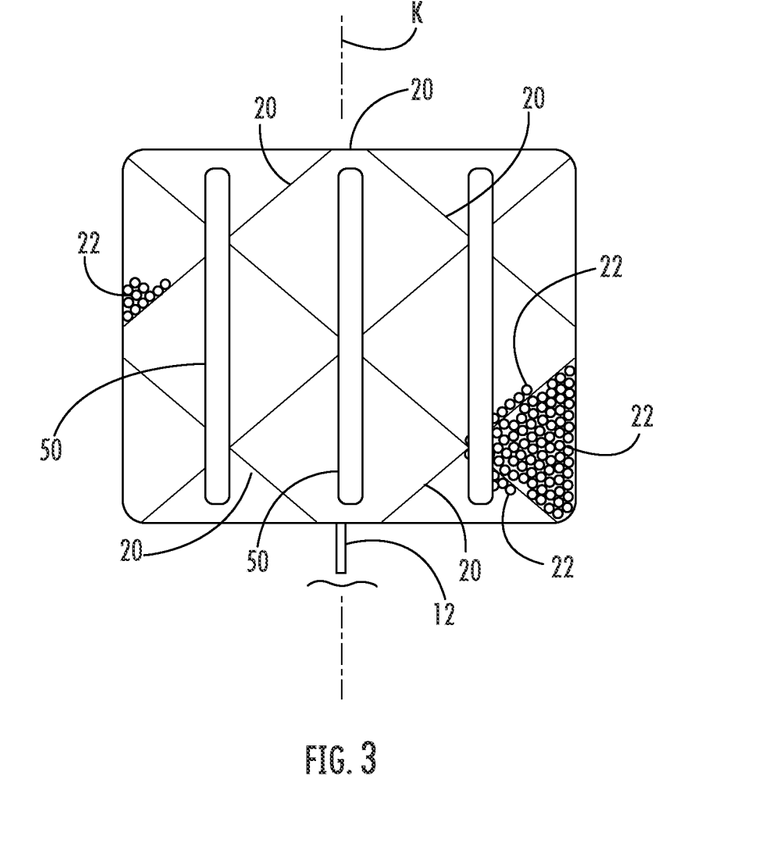
FIG. 3 illustrates at a distal end of wire is a deployed device designed to implement an endovascular treatment mesh with hydrogel coating, further including vertically oriented elements of reinforced mesh.

FIG. 3 also shows the nonspherical embodiment of treatment mesh (20) of the current invention, having hydrogel coating (22), and further including vertically oriented reinforcement members (50). In the preferred embodiment, all elements including reinforcement member (50) and wire (12) are coated with hydrogel (22). The treatment mesh 20 defines a longitudinal axis "k" and a longitudinal length extending along the longitudinal axis "k". As shown, in illustrative embodiments, the reinforcement members 50 extend relative to the longitudinal axis "k" for a major portion of the length of the treatment mesh 20.

In the foregoing embodiments, wire (12) may be included with or substituted by another endovascular delivery device (not shown) which, in the preferred embodiments, are also coated with hydrogel (22) in a thickness adapted to the size of the vasculature.

The present invention may be used according to the following method. To use the present invention to ameliorate aneurysm recurrences, amorphous hydrogel is deployed upon an intrasaccular occlusion device as follows:

(a) providing an insertion rod having a first end and a second end;

(b) said intrasaccular occlusion tool connected to the first end of the insertion rod;

(c) said intrasaccular occlusion tool having an outer surface and an inner surface;

(d) said outer surface coated with said amorphous hydrogel;

(e) said intrasaccular occlusion tool being moveable between a retracted position and a deployed position;

(f) inserting said intrasaccular occlusion tool and a portion of the insertion rod into the brain using arterial pathways while said intrasaccular occlusion tool is in a retracted position;

(g) deploying said intrasaccular occlusion tool inside an aneurism such that said intrasaccular occlusion tool is configured to provide a seal between said aneurism and said arterial pathway; and (h) securing the perimeter of said outer surface of said intrasaccular occlusion tool against a wall of said aneurism.

The present invention can alternatively be used by embedding or impregnating pharmaceutical compounds medications in a stent for local delivery, short release or sustained release using permanent nondegradable hydrogel or biodegradable hydrogel. The following are nonlimiting embodiments.

Placing a stent with chemotherapy embedded into carotid artery for a brain tumor in that vascular distribution, or in the right renal artery for a right kidney tumor, or in right pulmonary artery for a right lung mass. This could allow sustained delivery locally, while minimizing the systemic dose and associated side effects.

Similarly, to minimize the risk of severe symptomatic vasospasm in aneurysmal subarachnoid hemorrhage (a typical bleed from a ruptured brain aneurysm), a vasodilator that slowly releases over time can be embedded in a stent for placement in the common or internal carotid arteries on both sides, +/– placement in one or both vertebral arteries. Nonlimiting examples of vasodilators that can be embedded include nimodipine, verapamil, Cardene, nitroglycerin, and nitroprusside.

Although the invention has been described in detail in the foregoing embodiments and methods for the purpose of illustration, it is to be understood that such detail is solely for that purpose, and that variations can be made therein by those skilled in the art without departing from the spirit and scope of the invention, except as it may be described by the claims set forth in this application.

What is claimed is:

1. A device for ameliorating aneurysm recurrences, comprising:
 a deployable treatment mesh; and
 a plurality of substantially parallel vertically oriented elongated support reinforcements associated with the treatment mesh, the elongated support reinforcements being detached from each other, and extending substantially through the treatment mesh;
 wherein upon deployment of the deployment mesh and the elongated support reinforcements, at least an array of ends of the elongated support reinforcements are substantially oriented along a plane aligned with the opening of the aneurysm into which the device was deployed.

2. The device of claim 1, further comprising an amorphous hydrogel, wherein the hydrogel is impregnated with pharmaceutical compounds.

3. The device of claim 1, further comprising a thin coating of an amorphous hydrogel on any surface exposed to blood or a lumen wall.

4. A device for treatment of a bodily tissue, comprising:
 a treatment mesh configured to transition between a non-deployed condition and a deployed condition, the treatment mesh configured for insertion within bodily tissue when in the non-deployed condition and configured to expand, the treatment mesh defining a longitudinal axis and having a longitudinal length extending along the longitudinal axis; and
 a plurality of reinforcement members coupled to a wall of the treatment mesh, the reinforcement members each defining a length extending along a major portion of the length of the treatment mesh, the reinforcement members configured to provide structural support to the treatment mesh, adjacent members being spaced relative to each other.

5. The device of claim 4, wherein the reinforcement members are parallel with respect to the longitudinal axis of the treatment mesh when at least in one of the non-deployed, partially deployed and deployed conditions.

6. The device of claim 5, wherein the reinforcement members are parallel with respect to the longitudinal axis when in each of the non-deployed, partially deployed and deployed conditions.

7. The device of claim 5, wherein one or more of the reinforcement members are coated with hydrogel.

8. The device of claim 4, wherein at least a portion of the treatment mesh includes a coating of hydrogel, the hydrogel configured to expand in-vivo.

9. The device of claim 8, wherein a majority of an outer surface of the treatment mesh includes the coating of hydrogel.

10. The device of claim 8, wherein the treatment mesh includes hydrogel within an interior thereof.

11. The device of claim 4, wherein the treatment mesh includes one or more struts within an interior of the treatment mesh, the one or more struts comprising hydrogel.

12. The device of claim 4, wherein the reinforcement members comprise at least one of metal, metal alloys, plastic or a suitable stiff material.

13. The device of claim 4, wherein one or more of the reinforcement members are attached to the inside of the treatment mesh.

14. The device of claim 4, wherein one or more of the reinforcement members are attached to the outside of the treatment mesh.

15. The device of claim 4, wherein at least one reinforcement member is attached to the inside of the treatment mesh.

16. The device of claim 15, wherein at least one reinforcement member is attached to the outside of the treatment mesh.

17. The device of claim 4, including a delivery wire attached to one of the treatment mesh or a reinforcement member.

18. The device of claim 17, wherein the delivery wire comprises a hydrogel coating.

19. The device according to claim 4, wherein the treatment mesh is configured as at least one of an intravascular device configured to occupy an outpouching in a vascular organ, a stent, an intravascular device, a genitourinary tract device, a biliary tract device and a gastrointestinal device.

20. A device for treatment of an aneurysm, comprising:
a treatment mesh configured for insertion within body tissue, the treatment mesh defining a longitudinal axis and having a longitudinal length extending along the longitudinal axis; the treatment mesh including one or more reinforcement members coupled to a wall of the treatment mesh, the one or more reinforcement members having a rigidity greater than a rigidity of the treatment mesh and being configured to provide structural support to the treatment mesh, a given one of the one or more reinforcement members defining a length extending along a major portion of the length of the treatment mesh.

* * * * *